United States Patent [19]

Adams

[11] 4,347,840
[45] Sep. 7, 1982

[54] ORTHOPEDIC CORRECTIONAL SUPPORT SYSTEM

[75] Inventor: Gerald M. Adams, Huntsville, Ala.

[73] Assignee: Orthotech, Incorporated, Herkimer, N.Y.

[21] Appl. No.: 201,355

[22] Filed: Oct. 27, 1980

[51] Int. Cl.³ ............................ A61F 5/00; A47C 3/00
[52] U.S. Cl. ........................................ 128/70; 297/284
[58] Field of Search ..................... 128/68, 68.1, 69, 70; 297/284

[56] References Cited

U.S. PATENT DOCUMENTS

| | | |
|---|---|---|
| 32,013 | 4/1861 | Taylor . |
| 32,014 | 4/1861 | Taylor . |
| 32,015 | 4/1861 | Taylor . |
| 87,216 | 2/1869 | Southack .............................. 297/284 |
| 1,562,266 | 2/1922 | Todd . |
| 3,379,472 | 4/1968 | Hilfiker ............................... 297/284 |
| 3,565,482 | 2/1971 | Blodee ................................ 297/284 |
| 3,656,190 | 4/1972 | Regan et al. . |
| 3,717,376 | 2/1973 | Lutchansky . |
| 3,815,586 | 6/1974 | Kazik . |
| 3,877,750 | 4/1975 | Scholpp . |
| 3,990,742 | 11/1976 | Glass .................................. 297/284 |
| 4,033,339 | 7/1977 | Roberts et al. . |
| 4,033,567 | 7/1977 | Lipfert . |
| 4,085,738 | 4/1978 | Kodera . |
| 4,085,744 | 4/1978 | Lewis et al. . |
| 4,112,935 | 9/1978 | Latypov et al. . |
| 4,121,577 | 10/1978 | Binder . |
| 4,161,337 | 7/1979 | Ross et al. . |
| 4,190,286 | 2/1980 | Bentley . |

FOREIGN PATENT DOCUMENTS 1404659 6/1961 Fed. Rep. of Germany ...... 297/284
1216177 3/1970 United Kingdom ................ 297/284

OTHER PUBLICATIONS

Unidentified Publication, Article "Rebab Chair".
Unidentified Publication, Article "Trunk Support".
Medical Equipment Distributors, Inc., "Other Chairs for Children".
Herman L. Kamenetz, M.D., "The Wheelchair Book", Mobility for the Disabled, 1969. Ed.
Robert J. Trotter, "Preventing the Curve", Science News, vol. 115, pp. 298, 299 and 301, May 5, 1979.

Primary Examiner—Richard C. Pinkham
Assistant Examiner—Carl Moy
Attorney, Agent, or Firm—Roylance, Abrams, Berdo & Farley

[57] ABSTRACT

A chair for providing support and corrective forces to a patient having scoliotic, lordotic or kyphotic conditions includes parallel side panels with parallel vertical slots on the inner faces and slats extending between the panels. The slats have end fittings which are selectably insertable in the slots with the bottom of each slat resting on the one below so that the slats define a generally curvilinear surface having predetermined curvatures. Devices for holding straps and pads to apply lateral forces in a predetermined manner are also provided. Specific slat structure and full adjustability is provided.

9 Claims, 11 Drawing Figures

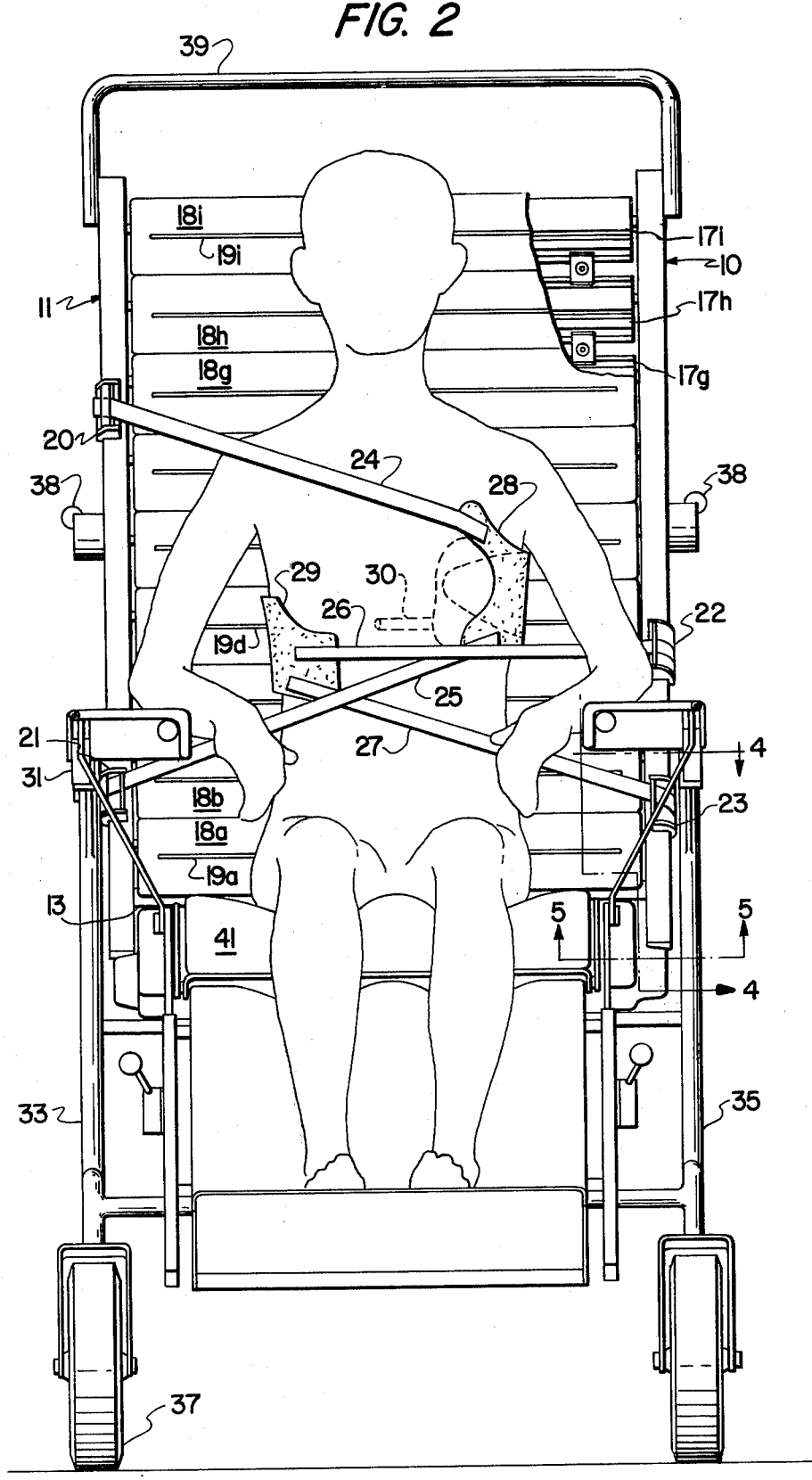

ORTHOPEDIC CORRECTIONAL SUPPORT SYSTEM

This invention relates to an apparatus for providing support for the body of a patient having a neurological or musculo-skeletal disorder or disease which affects the upper body and, in particular, the spine.

BACKGROUND OF THE INVENTION

There are numerous disorders or diseases which affect the back of a patient in varying degrees, from a mild abnormal variation to severe, crippling and functional disablement. The term "scoliosis" has been applied to a group of such disorders and there are numerous varieties of scoliosis having different causes, some resulting from diseases and others being symptomatic of muscular weakness. The common, obvious manifestation of scoliosis is lateral curvature of the spine, usually compound curvature, and in the more severe cases the afflicted patient is unable to walk or even to sit up. In other cases, the patient who is ambulatory can be assisted by mechanical support such as the "Milwaukee Brace" which has been used for several years.

There are also other musculo-skeletal disorders which affect the spine or muscular structure of the upper body and particularly the back and which can be functionally disabling such as lordoctic or kyphotic skeletal anomalies. These will not be discussed in any detail, being well known to medical practitioners.

A common characteristic of advanced progressions of these illnesses is that the patient cannot sit, walk or move about normally, and sometimes not at all, resulting in progressive degradation of muscle tone and other body functions, requiring considerable care and assistance, and also resulting in severe and possibly irreparable psychological harm.

Various padded beds and wheelchairs have been devised to assist such patients and to give them degree of comfort and mobility. These have, generally speaking, not differed significantly from conventional wheelchairs except in the degree of padding and in providing extra support for the head or trunk.

They have, however, not been specifically adaptable to the necks of individual patients and have not been adjustable in such a way that a treating physician can prescribe sets of forces or supports for a patient in such a way that the supports and forces can be applied to the patient by, for example, a physical therapist.

Examples of prior art devices and some discussions of the problems are found in the following documents.

Medical Equipment Distributors, Inc. *"Other Chairs for Children"*

Herman L. Kamenetz, M.D., *"The Wheelchair Book"*, Mobility for the Disabled, 1969, ED.

Robert J. Trotter, *"Preventing the Curve"*, Science News, Vol. 115, pgs. 298,299 and 302, May 5, 1979

| | |
|---|---|
| 1,562,266 | Todd |
| 3,656,190 | Regan et al. |
| 3,717,376 | Lutchansky |
| 3,815,586 | Kazik |
| 3,877,750 | Scholpp |
| 3,990,742 | Glass et al. |
| 4,033,339 | Roberts et al. |
| 4,033,567 | Lipfert |
| 4,085,738 | Kodera |
| 4,085,744 | Lewis et al. |
| 4,112,935 | Latypov et al. |
| 4,121,577 | Binder |
| 4,161,337 | Ross et al. |

BRIEF DESCRIPTION OF THE INVENTION

An object of the present invention is to provide a support structure, such as a chair, which has provision for external support of the axial skeleton of a patient with independently adjustable anterior, posterior and lateral adjustments.

A further object is to provide such a support system in which the nature of the various support forces is prescribable by a position and is reproducible.

Yet another object is to provide a support chair system for a patient which permits limited anterior-posterior movement of the patient.

A still further object is to provide such an apparatus which includes, or can include, various comfort and convenience features without detracting from corrective forces applied to the body of the patient, and which is constructed to permit extended occupancy by a patient, and which is simple and effective to use, clean and maintain.

Briefly described, the invention includes an orthopedic chain having a back structure comprising a plurality of elongated slat-like members extending laterally across the chair back, each of said members having a front surface; means on the longitudinal edges of the slat-like members for interconnecting the members in edge-two-edge articulated relationship; first and second support panels at opposite sides of said chair back; and means on the inwardly facing portions of each of the support panels defining a plurality of recesses for receiving the end of the slat-like members, said members being insertable between said panels with the ends of the members in pairs of said recesses and with said members in edge-to-edge relationship in a selectable pattern of anterior-posterior locations so that the front surfaces of said members define a preselected curvilinear surface.

In order that the manner in which the foregoing and other objects are attained in accordance with the invention can be understood in detail, particularly advantageous embodiments thereof will be described with reference to the accompanying drawings, which form a part of this specification and wherein:

FIG. 2 is a front elevation of a support system in accordance with the invention;

Figure 1:
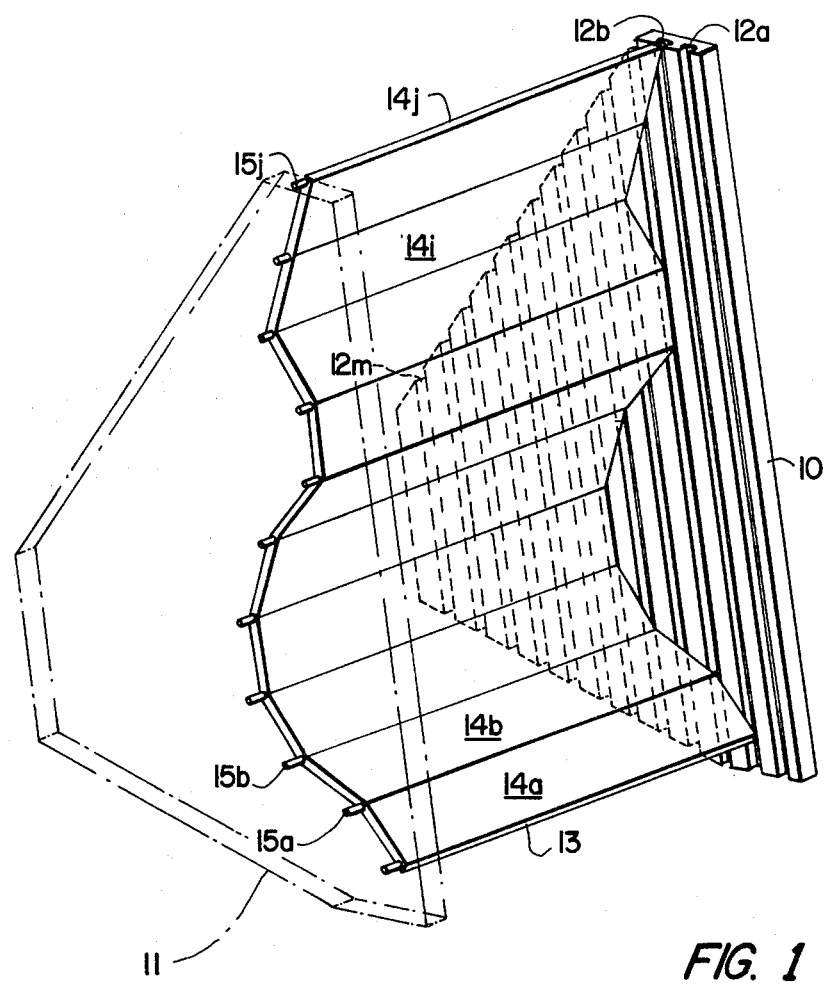
FIG. 1 is a simplified schematic perspective view of a support structure in accordance with an aspect of the present invention for illustrating the principal thereof.

The simplified schematic illustration of FIG. 1 will be used to discuss and explain the principals on which the support system of the present invention are based. As shown therein, the simplified structure includes a side panel 10 and a side panel 11, panel 11 being shown only in phantom outline to permit illustration of other features of the structure. The two panels are generally similar in construction, one being a mirror image of the other. The panels are supported in parallel relationship and would normally extend in parallel, vertical planes. Panel 10 is provided with a series of generally vertically extending parallel grooves 12a, 12b, . . . 12m. It will be assumed that the inwardly facing surface of panel 11 is provided with similar grooves. A fixed rod 13 extends between panel 10 and panel 11. As illustrated, the rod extends from a location near the bottom of groove 12b to point near the bottom of the similar groove in panel 11, the ends of the rod being fixedly attached to the panels in the groove. A plurality of slat-like members 14a-14j extend between the panels and form the primary support surface for the back of a patient. Thus, the structure shown in FIG. 1 can be viewed as the generally upwardly extending back portion of a chair. Each of members 14a-14j is provided with a recess along its lower edge and a generally curved surface at its upper edge so that when one slat is placed atop another, there is an articulated relationship there between. The precise nature of this structure will be discussed in conjunction with the following figures. Additionally, near the upper end of each slat-like member 14a-14j is an axial extension 15a-15j which is illustrated in FIG. 1 as being a rod-like extension dimensioned to be closely received in grooves 12a-12m and the similar grooves in the opposed panel. Although not visible in FIG. 1, the rods extend from both ends of each slat-like member.

The structure initially exists with the two panels and rod 13 interconnected. Assembly of the slat portion is then commenced by inserting slat 14a between panels 10 and 11 with rod 15a inserted in one pair of grooves which, in the illustrated situation, would include groove 12c in panel 10 and the corresponding groove in panel 11. This rod is then permitted to slide to the bottom of the structure with the lower, convex, edge of panel 14a resting on rod 13. Slat 14b is then inserted with its extensions 15b in one of the slots and with the lower edge of that slat resting on the upper edge of slat 14a. Although extensions 15b are shown as being inserted in slot 12e in panel 10 and the counterpart slot in panel 11, it will be recognized that those extensions could have been inserted in any one of slots 12a-12e, depending upon the angle of repose desired for that slat. Each of the subsequent slat is then inserted, in sequence, and it will be recognized that the slots selected for insertion of the extensions 15a-15j at the ends of the slats can follow a selectable pattern of anterior-posterior locations so that the front surfaces of the slat-like members 14a-14j define a curvilinear surface with each slat resting on the one before, the front surfaces of the slats being those surfaces predominately visible in FIG. 1. A segmented cushion can then be affixed to these front surfaces for added patient comfort, and the total surface thus defined can be established in accordance with a predetermined curvature necessary for proper support of the patient's back.

It should be mentioned that the surface established by the slot selection pattern in FIG. 1 is intended only for purposes of discussion and does not necessarily illustrate a surface which would be usable in the treatment of a patient.

As will be further recognized, the panels 10 and 11 could be rectangular in overall shape, but the generally trapezoidal configuration illustrated represents a saving in material costs and provides locations for the patterns most often required.

A major advantage of the concept illustrated in FIG. 1 is that the positions of the upper ends of the slats can be specified to establish any one of a wide variety of curved surfaces simply by identifying, as by number or letter, the slot in which the extensions 15a-15j of each panel are to be inserted. Thus, a physician treating a patient having a specific skeletal disorder, knowing the horizontal spacing of the slots and the slat width, can specify a curvature which is most advantageous for proper support of the condition being treated.

Thus, if desired, the patient can be moved from the chair to a bed and returned to the same or a different chair, and the proper curvature can be checked or reestablished without requiring additional attention by the physician. It is only necessary to have the prescription for the pattern available in order to be sure that the proper curvature is being established.

In addition, this structure, along with features to be described hereinafter, permits the establishment of lateral support for the patient in a manner which is, similarly, prescribable and reproducible.

Figure 3:
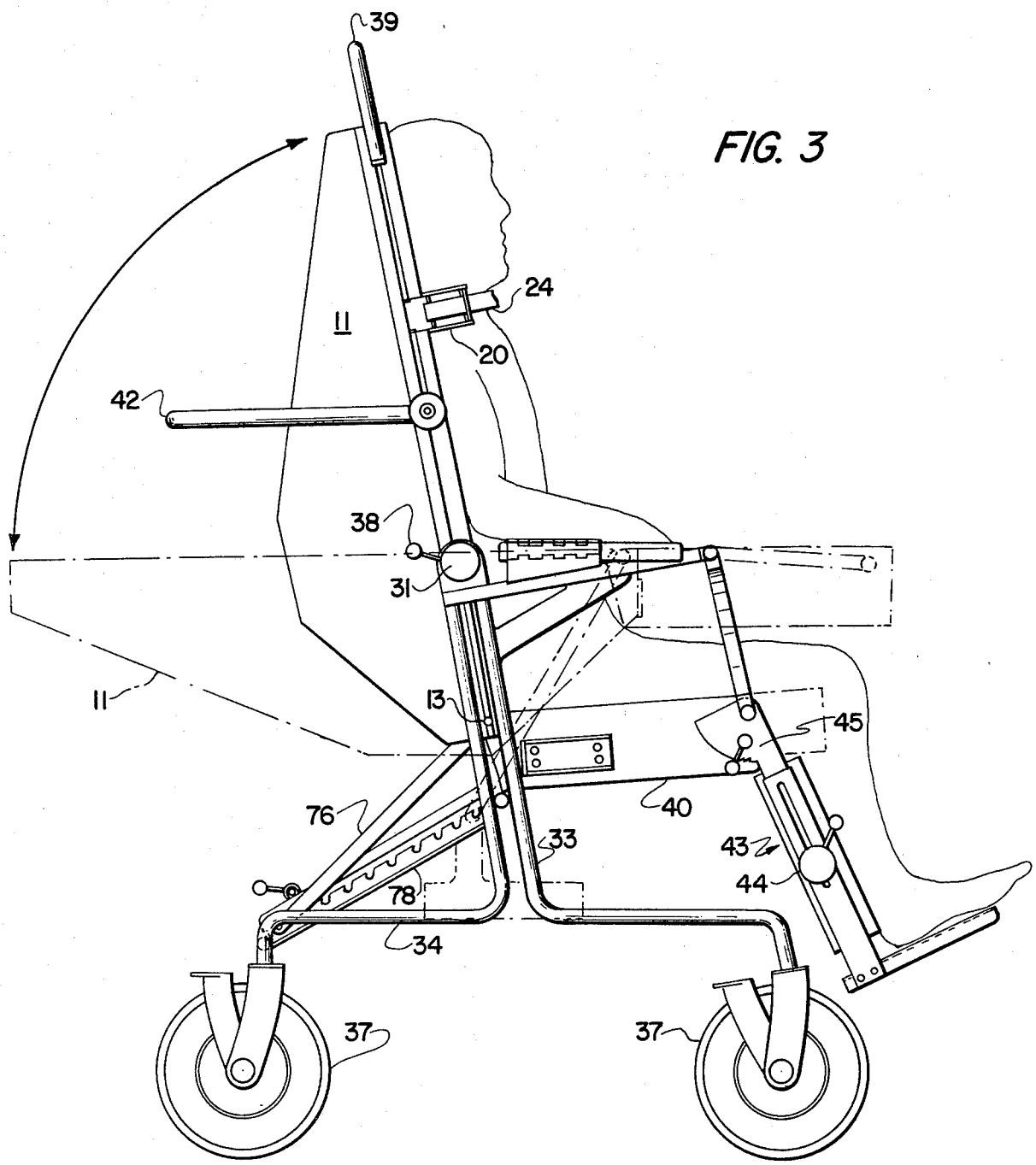
FIG. 3 is side elevation of the apparatus of FIG. 2.

FIGS. 2 and 3 show, in front and side elevation, respectively, a practical embodiment of an apparatus employing the principal shown in FIG. 1 together with the provision of lateral support forces. As seen in these figures, side panels 10 and 11 are interconnected by a rod 13 extending between the lower portions thereof, with slat-like members 17a-17i extending between the side panels, the slats being covered by a segmented cushion having segments 18a-18i. The slat-like members, although following the principal discussed in connection with FIG. 1, are of somewhat different construction in detail, each slat having an elongated central slot 19a-19i extending therethrough and aligned with similar slots in the cushions. Side panels 10 and 11 have forward rail structures which permit the attachment and adjustment of sling retaining members 20, 21, 22 and 23 for attachment of straps 24-27, respectively, the other ends of these straps being connected to support pads 28 and 29. Opposite edges of the pads are connected to straps such as strap 30 which is behind the patient and which passes through a slot, such as slot 19d and is attached in the back of the chair, as will be described.

The back structure including side panels 10 and 11 and slats 18a-i is pivotably connected by axles 31, 32 to a frame structure including tubular struts 33, 34, 35 and 36 to which wheels 37 are attached to render the structure mobile. Additionally, the back structure is pivotably connected to a seat pan 40 containing a cushion 41, this assembly being movable to a horizontal patient supporting system as illustrated in phantom lines in FIG. 3, the position being adjustable by a clutch associated with the axles and operated by handles 38.

A lifting handle 39 extends between the top of panels 10 and 11, and a pushing handle 42 can also be provided, the ends of handles 39 and 42 being attached in grooves on side rails is pivotally attached to seat pan 40 and the arm structure and is adjustable in height and angle by mechanisms 44 and 45. These features and adjustments, while highly desirable, are not critical to the present invention and will therefore not be described in further detail.

Figure 4:
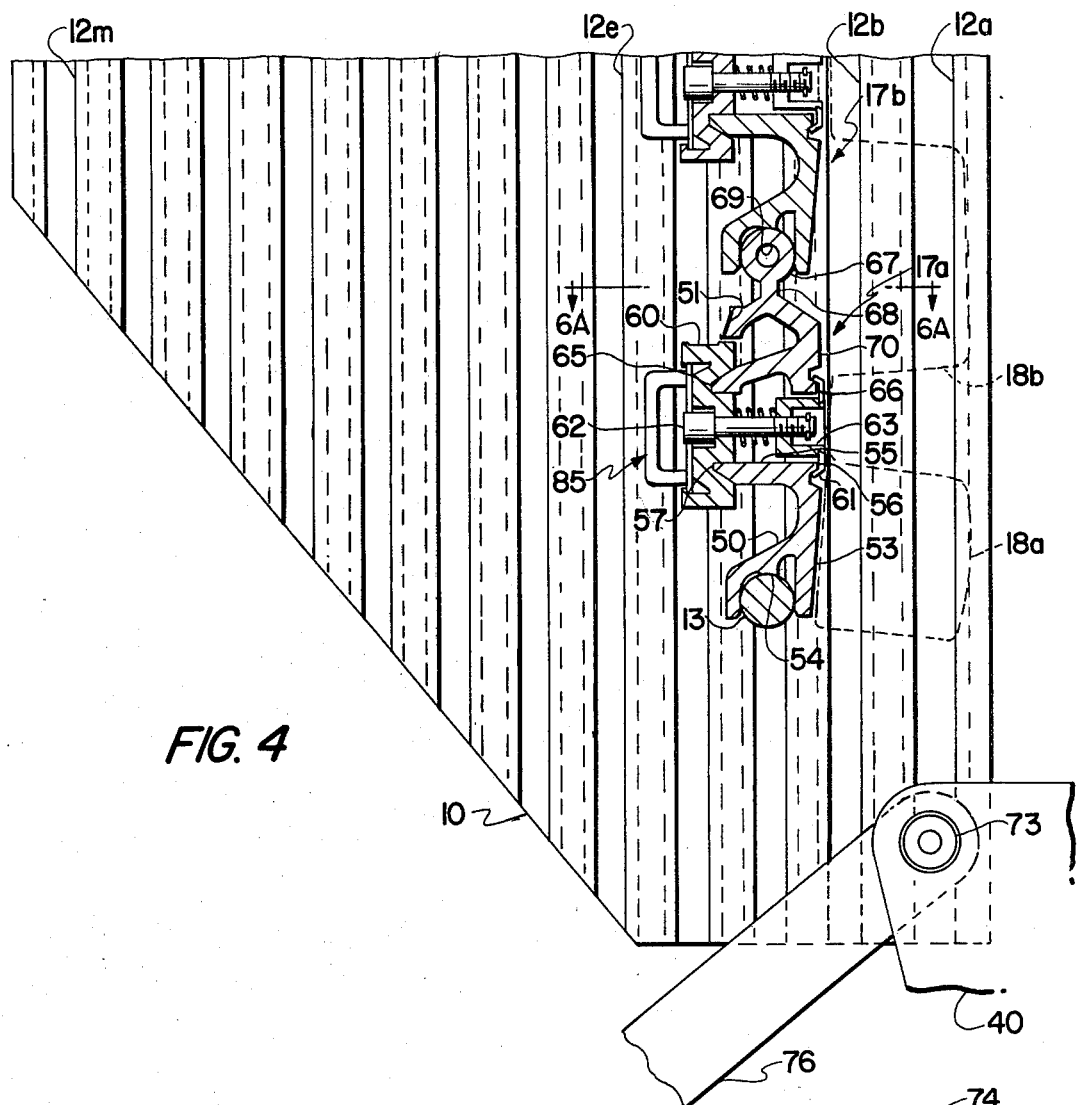
FIG. 4 is a partial side elevation, in partial section, along line 4—4 of FIG. 2.
Figure 5:
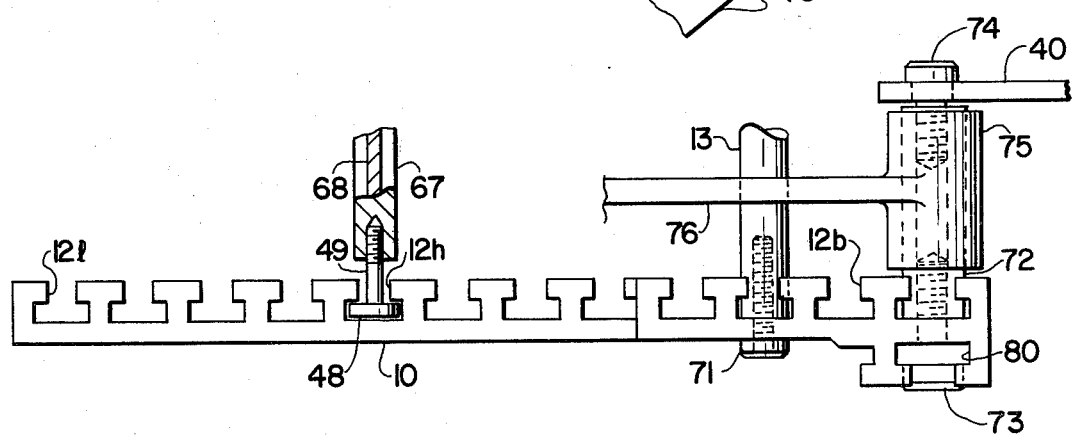
FIG. 5 is a partial bottom plan view along line 5—5 of FIG. 2.
Figure 7:
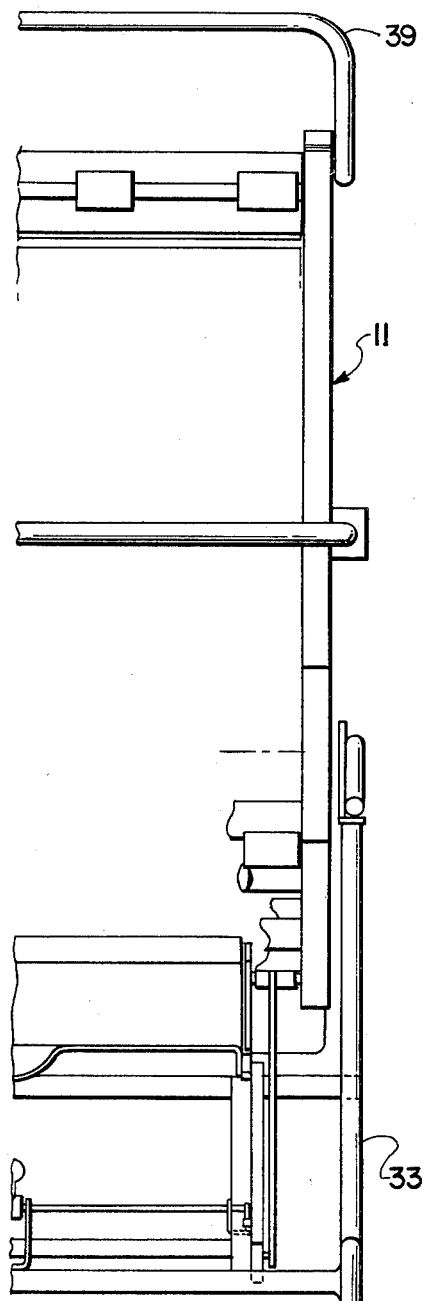
FIG. 7 is a partial rear elevation of the apparatus of FIGS. 2 and 3.

The details of the slot structure can be more clearly seen in FIGS. 4 and 5 which show panel 10 with slots 12a–12l, only the lower portion of the panel being illustrated in FIG. 4. As seen in FIG. 5, slots 12a–12m are T-shaped to receive the head 48 of a T-shaped support pin 49, shown by way of example in slot 12h.

Because the slats are identical, only one will be described. As seen in FIG. 4, each of the slats such as 17a comprises two elongated extruded rails 50 and 51. While the exact cross-sectional shape of the rails can vary, there are certain characteristics of importance. Lower rail 50 has a substantially flat front surface 53, a generally concave elongated recess 54 which opens downwardly to receive rod 13 (or, in the case of the upper slats, the top of the next lower slat), and a generally flat top surface 55. Surface 55 terminates in front and rear flanged edges 56 and 57 which are engaged by a locking slide assembly including a block 60 having a longitudinal groove shaped to receive edge 57 and a latch plate 61 having an inwardly bent edge to engage edge 56. Block 60 and plate 61 are held together by an allen head cap screw 62 the head of which seats in a recess in block 60 and the threaded end of which threadedly engages an opening in a cylindrical mounting cup 63 which is fixedly attached to plate 61. A compression coil spring 64 urges cap 63 away from block 60 so that the longitudinal position of the block relative to the rails can be adjusted with slight loosening of screw 62. The length of block 60 is significantly less than the lengths of the rails, being in the order of 3" to 5", and at least two such blocks are normally provided for each slat assembly.

Upper rail 51 has a rear edge 65 which is received in a second longitudinal groove in block 60 and a front flanged edge 66 which is engaged by plate 61 in the same manner as edge 56. The top of rail 51 terminates in a cylinder 67 which is connected to the body of the rail by a web 68. Cylinder 67 has a central bore 69 to receive pin 49. Preferably, bore 69, which need not extend entirely through cylinder 67, is internally threaded to receive the externally threaded end of pin 49. Rail 51 also has a front surface 70 which, together with surface 53 of rail 50, forms the front surface of the slat assembly. Surfaces 53 and 70 can be provided with one part of a hook and loop fastening fabric, such as that sold under the trademark VELCRO, the mating fabric being attached to the back of the cushions 18a–i so that, after placement of the slots, the cushions can be attached to the curvilinear surface.

As seen in FIG. 5, rod 13 is fixedly attached to panel 10 by a machine screw 71 which passes through plate 10 at slot 12c and into a threaded hole in the end of the rod. A similar attachment is provided at panel 11. At the front edge of panel 10 a short axle 72 is attached near the bottom of slot 12a by a screw 73, pan 40 being attached to the other end thereof by a screw 74. A sleeve 75 is rotatably carried by axle 72, sleeve 75 having a bar 76 attached thereto. As seen in FIG. 3, bar 76 and a similar bar on the other side of the chair are interconnected by a rod which can be placed in any one of a plurality of notches in a diagonal brace 78 to establish the angle of the back structure.

Also at the front of panel 10 and on the outer surface thereof is a T-shaped slot 80 which can receive support pins similar to pin 49 to hold strap retainer 20 and handles 39 and 42. With suitable locking devices, these articles can be adjusted to any desired position. Slot 80, and a similar slot on the outside front portion of panel 11, can also be used to attach additional devices such as traction equipment, exercise bars and the like.

Figure 6A:
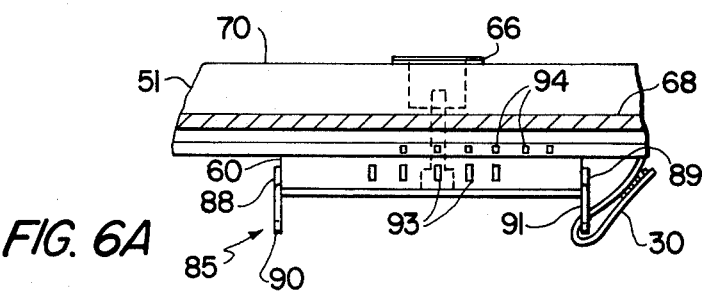
FIG. 6A is an enlarged partial plan view along line 6A—6A of FIG. 4.
Figure 6B:
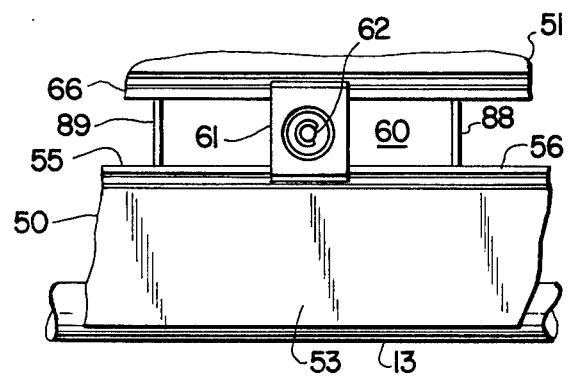
FIG. 6B is an enlarged partial front elevation of the structure shown in FIG. 6A.
Figure 6C:
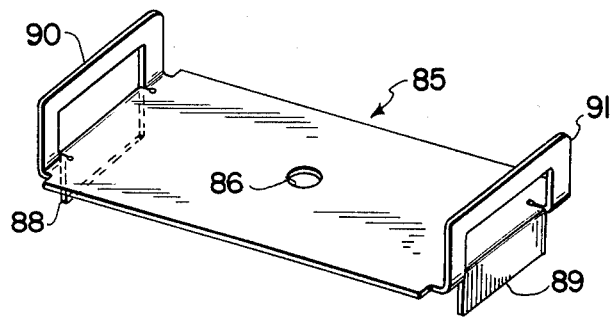
FIG. 6C is a perspective view of a portion of the structure of FIGS. 6A and 6B.

A strap retaining plate 85 is attached to block 60, this plate being visible in FIG. 4 and more clearly seen in FIGS. 6A, 6B and 6C. Plate 85 has a central opening 86 to permit insertion of, and access to, screw 62. Parallel side edges of plate 85 are received under shoulders formed in the longitudinal back edges of block 60 as seen in FIG. 4. The ends of plate 85 are cut along a U to form locking tabs 88 and 89 and also to form upstanding u-shaped strap-holding loops 90 and 91. Tabs 88 and 89 are bent about 90 along the opposite ends of block 60, at least one of those tabs being left unbent until plate 85 is slid into position on block 60. Loops 90 and 91 are bent about 90 in the opposite direction and therefore protrude rearwardly relative to the chair back.

As seen in FIG. 6A, the upper surface of block 60 has one or more calibration marks 93 which can be aligned with similar calibration marks 94 on the rear of rail 51. Marks 94 can be numbered in any convenient fashion to identify longitudinal position of the blocks, and therefore loops 90 and 91, along the rails. These numbered marks can thus serve as the basis for a portion of the prescription prepared by an attending physician.

A strap, such as strap 30 of FIG. 1, can be passed through the slot between rails 50 and 51 forming a slat assembly, and can be looped upon itself around one of loops 90 and 91, as shown in FIG. 6A. The strap can be provided with VELCRO fastening material or the like or some other convenient fastener.

Figure 9:
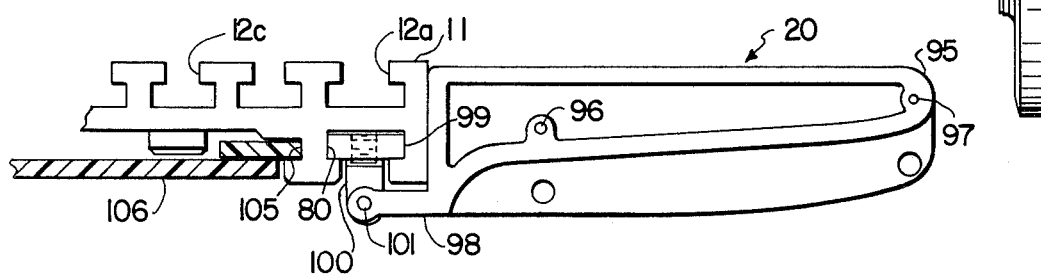
FIG. 9 is an enlarged partial plan view along 9—9 of FIG. 2.
Figure 8:
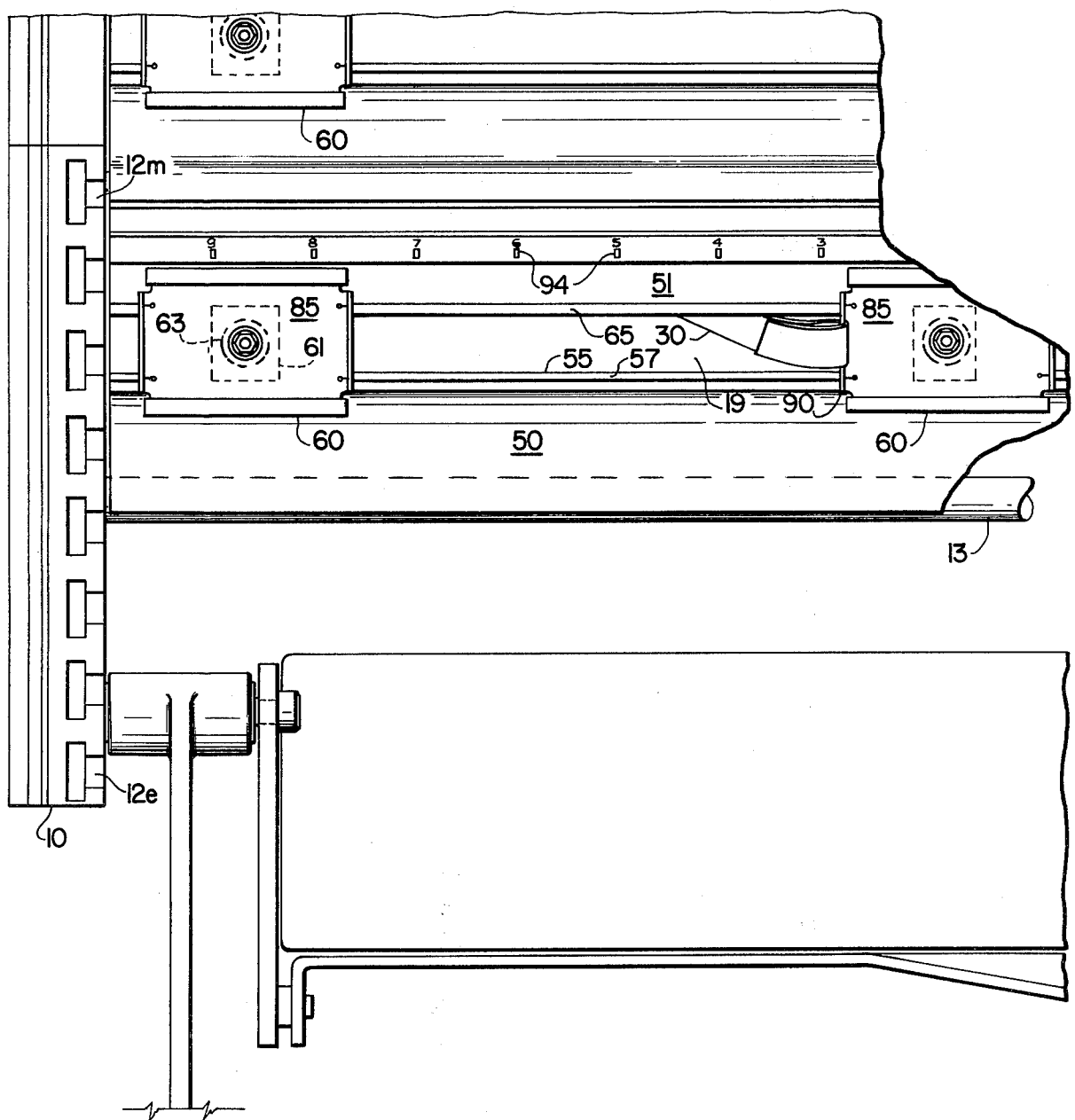
FIG. 8 is an enlarged rear elevation of the apparatus of FIGS. 2, 3 and 7.

FIGS. 8 and 9 show portions of the assembled chair structure from the back and illustrate the relationship of blocks 60 and plates 85 holding together portions 50 and 51 of the bottom slat assembly which rests on rod 13. The bottom of panel 10 is also visible, the lower open ends of slots 12e–12m being visible because of the slope provided at the rear of panel 10. Also visible is the indicia 94 on rail 51 for positioning blocks 60 and the loops of plates 85.

FIG. 9 shows, in top plan view, a portion of the front of panel 11 with a strap retainer 20 which includes upper and lower identical plates 95 having openings 96 and 97 to receive generally vertically extending pins around which an end of straps such as straps 24, 25 and 26 can be passed. An extension 98 from the outer, rear portion of the plates holds them together and forms an L-shaped surface which conforms to the front of the panel. An elongated plate 99, dimensioned to be received in slot 80, has two outwardly protruding lugs 100, one being visible in FIG. 9, to which extension 98 is pivotally connected by a hinge pin 101. Locking screws 102 are threadedly received in plate 99 and can be tightened to protrude against the inner surface of slot 80, forcing plate 99 outwardly against the inner flanges of the slot, thereby locking the assembly in position. The hinged connection of extension 98 to lugs 100 permits the retainer to be swung out of the way when, for example, a patient is being placed in or removed from the chair.

It will be observed in FIG. 9 that an elongated recess 105 is formed to the rear of slot 80. This slot is to receive the front edge of a cover 106 which can be molded from plastic in a shape to cover panels 10 and 11 and the back of the seat structure. The cover is, of course, attractive in appearance but also performs the function of inhibiting unauthorized individuals from altering the adjustments of the straps or blocks 60.

While it is believed that the utility and manner of use of the apparatus disclosed herein will be apparent from the foregoing discussion, following is a brief description of a procedure.

Initially, a physician would normally arrive at an analysis of the abnormal curvatures of the spine of a patient and define, from that analysis, the curvature and support which will allow the patient to be comfortably supported and which will tend to halt progression of the condition. Factors including the age and general physical condition are also considered. The physician can then specify slot locations for the top of each slat to form the chair back structure. For this purpose, the side panel slots can be identified by a sequence of letters, for example, and the slats by number. Thus, the configuration shown in FIG. 1 could be prescribed by the sequence 1C, 2E, 3F, 4F, 5E, 6C, 7C, 8D, 9C, 10B.

The lateral support is then defined by specifying the positions of retainers 20, the positions of loop retainers 90 and 91, and the number and lengths of the interconnecting straps and pads. For purposes of defining the positions of retainers 20, the front surfaces of panels 10 and 11 can also be provided with numbered indicia, although the position can also be defined by its relationship to certain ones of the slats or by measurement from the top of the side panel on which it is mounted.

The pads 28, 29 and straps 24–27 are then cut from the material of a type normally used by physicians for making custom slings, soft casts and the like, to fit the physical characteristics of the individual patient. This is the most subjective part of the procedure and would likely be done by, or under the direct supervision of, the physician. Once, the pads have been cut and joined to the straps, and the straps have been passed through the retainers 20 and loops 90 and 91 and cut to proper length, they can be marked so that they can be removed and restored to the same positions. The pads and straps can, most conveniently, be joined by VELCRO fasteners.

The apparatus thus described is perferably formed using materials such as aluminum and stainless steel for the metal portions and polymeric materials for the nonmetallic parts so that it can be subjected to cleaning using hot showers and detergents without degradation. All portions of the apparatus have been designed to avoid areas which might tend to collect water or other liquids and to avoid "corners" permitting bacterial growth.

The seat pan and frame are also constructed so that receptors for waste material can easily be added, allowing use of the chair with incontintent patients.

While certain advantageous embodiments have been chosen to illustrate the invention it will be understood by those skilled in the art that various changes and modifications can be made therein without departing from the scope of the invention as defined by the appended claims.

What is claimed is:

1. An orthopedic chair having a back structure comprising
   a plurality of elongated slat-like members extending laterally across the chair back, each of said members having a front surface;
   means on the longitudnal edges of said slat-like members for interconnecting the members in edge-to-edge articulated relationship;
   first and second support panels at opposite sides of said chair back; and
   means on the inwardly facing portions of each of said support panels defining a plurality of recesses for receiving the ends of said slat-like members,
   said members being insertable between said panels with the ends of said members in pairs of said recesses and with said members in edge-to-edge relationship in a selectable pattern of anterior-posterior locations so that the front surfaces of said members define a preselected curvilinear surface.

2. An apparatus according to claim 1 wherein said means defining said plurality of recesses includes
   a plurality of generally vertically extending parallel slots in each of said panels.

3. An apparatus according to claim 2 wherein each of said slat-like members includes
   an extension at each end of the upper edge thereof dimensioned to be received in any one of said slots.

4. An apparatus according to claim 1 wherein each of said slat-like members further includes
   a loop means attached to said slat-like member for receiving an end of a strap,
      said loop means being slidably movable longitudinally on said slat-like member; and
   means for locking said loop means against longitudinal movement at any of a plurality of positions along said slat-like member, so that a strap can be extended from one of said loop means around the body of a patient occupying the chair and to the same or a seond one of said loop means.

5. An apparatus according to claim 4 wherein each said loop means is attached to its associated slat-like member on the back surface thereof,
   and wherein each said slat-like member includes
   means defining an elongated opening through said slat-like member to permit passage of straps therethrough.

6. An apparatus according to claim 4 and further comprising
   strap retainer means on at least one of said panels for receiving and holding an end of a strap.

7. An apparatus according to claim 1 wherein said back structure further includes
   a rod extending between a pair of said recesses near the lower end of said panels.

8. An apparatus according to claim 7 wherein each of said slat-like members comprises
   a first, lower, rail of substantially uniform cross-section along its length, said lower rail having
      a flat surface forming a portion of said front surfaces, and
      a downwardly open concave recess along the lower edge thereof;
   a second, upper rail of substantially uniform cross-section along its length, said upper rail having
      a flat surface forming the remaining portion of said front surface, and
      a generally cylindrical upper surface shaped and dimensioned to mate with the recess along the lower rail of an adjoining slot-like member; and
   at least one locking member attached to and interconnnecting said upper and lower rails for holding said rails in a substantially fixed, parallel spaced relationship with respect to each other.

9. An apparatus according to claim 8 wherein the lower portion of said upper rail and the upper portion of said lower rail are each provided with longitudinally extending flanges and wherein said locking member includes means for engaging said flanges.

* * * * *